United States Patent
Turkdogan

(12) 
(10) Patent No.: US 6,340,418 B1
(45) Date of Patent: Jan. 22, 2002

(54) SLAG OXYGEN SENSOR

(76) Inventor: Ethem T. Turkdogan, 5820 Northumberland St., Pittsburgh, PA (US) 15217

( * ) Notice: Subject to any disclaimer, the term of this patent is extended or adjusted under 35 U.S.C. 154(b) by 0 days.

(21) Appl. No.: 09/513,837

(22) Filed: Feb. 25, 2000

Related U.S. Application Data

(60) Provisional application No. 60/122,190, filed on Mar. 1, 1999, and provisional application No. 60/122,811, filed on Mar. 4, 1999.

(51) Int. Cl.[7] ............................................. G01N 27/30
(52) U.S. Cl. ..................... 204/400; 204/291; 204/292; 204/293; 205/775
(58) Field of Search ................ 204/400, 422, 204/423, 291–293; 205/775

(56) References Cited

U.S. PATENT DOCUMENTS

| | | |
|---|---|---|
| 3,141,835 A * | 7/1964 | Rolin et al. |
| 4,098,651 A * | 7/1978 | Alder |
| 4,342,633 A | 8/1982 | Cure |
| 4,627,892 A | 12/1986 | Worrell et al. |
| 4,657,641 A | 4/1987 | Nakamura et al. |
| 4,708,783 A | 11/1987 | Nakamura et al. |
| 4,717,463 A | 1/1988 | Clauss |
| 4,749,466 A | 6/1988 | Masson et al. |
| 4,786,374 A | 11/1988 | Worrell et al. |
| 5,112,456 A | 5/1992 | Worrell et al. |
| 5,223,125 A | 6/1993 | Clauss, Jr. et al. |
| 5,342,489 A | 8/1994 | Iwase et al. |
| 5,495,176 A * | 2/1996 | Shiranita et al. |
| 5,580,439 A * | 12/1996 | Baucke et al. |
| 5,596,134 A | 1/1997 | Phillippi et al. |
| 5,792,329 A | 8/1998 | Curé et al. |
| 5,989,408 A | 11/1999 | Baerts et al. |
| 6,013,163 A * | 1/2000 | Hsia et al. |

OTHER PUBLICATIONS

Horsley, "Some Experiments on Galvanic Cells Using Solid Electrolytes", AERE–R3427, (1961) month unavailable, pp. 1–14 and figure 2.*

Meszaros, G.A. et al. "Implementation of a Ladle Slag Oxygen Activity Sensor to Optimize Ladle Slag Practices at the U.S. Steel Mon Valley Works", *Iron ans Steelmaker*, 1997 month unavailable, 24(7) pp. 33–39.

* cited by examiner

*Primary Examiner*—T. Tung
(74) *Attorney, Agent, or Firm*—Akin, Gump, Strauss, Hauer & Feld, L.L.P.

(57) ABSTRACT

An electrochemical sensor for insertion into slag for determining the activity of a metal oxide in the slag is disclosed. The sensor includes a reference electrode comprising a mixture of a metal alloy and a metal oxide, the metal alloy and the metal oxide each being exposed on a surface of the reference electrode. The sensor also includes at least one oxide electrode comprising a mixture of a metal alloy and a metal oxide different from the mixture of the reference electrode, the metal alloy and the metal oxide of the oxide electrode each being exposed on a surface of the oxide electrode. The sensor further includes a refractory housing holding the reference electrode and each oxide electrode. The reference electrode and each oxide electrode extend from the refractory housing such that the surface of the reference electrode and the surface of the oxide electrode are each in direct contact with the slag when the sensor is inserted into the slag.

10 Claims, 5 Drawing Sheets

SLAG OXYGEN SENSOR

CROSS REFERENCE TO RELATED APPLICATIONS

This application claims the benefit of U.S. Provisional Application No. 60/122,190, filed Mar. 1, 1999, entitled "Theoretical Concept on Slag-Oxygen Sensors to Measure Oxide Activities Related to FeO, $SiO_2$ and CaO Contents of Steelmaking Slags" and U.S. Provisional Application No. 60/122,811 filed Mar. 4, 1999 entitled "Concept of Slag-Oxide EMF Sensors to Measure Oxide Contents of Molten Slags and Glasses".

BACKGROUND OF THE INVENTION

This invention relates generally to a device for measuring the electrochemical activity of a molten slag layer lying on a molten bath of metal, and more particularly, to a sensor for measuring the oxygen potential of oxides present in the slag.

Impurities in pig iron, from which steel is made, consist of carbon, manganese, phosphorus, silicon and sulfur. The concentrations of the aforementioned impurities have a major impact on the characteristics of finished steel. Thus during the refining of molten steel, it is necessary to periodically assess the molten steel for the concentration of the aforementioned impurities.

Conventionally, the concentration of impurities in the molten steel is determined by chemical analysis. The preparation of a sample of the molten steel to conduct the chemical analysis requires taking a sample of the molten steel and allowing the sample to solidify, followed by polishing and washing the sample. The relatively large amount of time required to prepare a sample of molten steel for chemical analysis seriously impacts the ability to correct an undesirable concentration of impurity thus found, particularly in the latter stages of the refining process.

In studies of plant data on slag and steel samples taken at vessel turndown, it has been found, with respect to reactions involving iron oxide in slag, that the slag/steel distribution ratios of phosphorus and sulfur in basic oxygen furnace (BOF) and quick basic oxygen (Q-BOP) steel making processes are scattered about the slag-steel equilibrium values. Further studies indicate consistent inter-relationships between the concentrations of FeO, $SiO_2$ and CaO in the slag at the end of the oxygen blow and the concentrations of sulfur and phosphorus in the molten steel, in both the BOF and Q-BOP processes. Thus, by rapidly determining the concentration of FeO, $SiO_2$ and CaO in the slag, in real time, near the end of the oxygen blow, corrective steps can be taken by appropriate flux additions to further dephosphorization and desulfurization of steel during the production of the steel.

The activity $a_{ox.}$ of a molten oxide in molten slag is defined by the expression:

$$a_{ox.} = \left(\frac{p_{o_2}ox.}{p_{o_2}^o ox.}\right)^{1/2}, \quad (1)$$

where $p_{o_2}$ ox. is the oxygen partial pressure of the slag in equilibrium with the actual liquid oxide in the slag and $p_{o_2}^o$ ox. is the oxygen partial pressure of the slag in equilibrium with pure liquid oxide.

Substantial amounts of experimental data have been collected over the years that relates the activity of FeO, $SiO_2$ and CaO in slag to the concentrations of the aforementioned metal oxides in the slag. Consequently, by measuring the activities of FeO, $SiO_2$ and CaO in slag, the concentrations of FeO, $SiO_2$ and CaO in the slag can be determined.

When an electrochemical sensor comprising two dissimilar (metal alloy+metal oxide) electrodes is immersed in molten slag or glass, there is created a difference in oxygen potentials at the slag-electrode interface between the two electrodes. The difference in oxygen potentials establishes an open circuit cell electromotive force (emf) by galvanic action that is a measure of the particular metal oxide activity of the slag. The open circuit emf of the galvanic cell thus formed by the two electrodes in contact with the molten slag can be expressed by the following well known thermodynamic relation:

$$\frac{10.08 \cdot E \text{ (mv)}}{T} = \log(p_{o_2}ox.)^{1/2} - \log(p_{o_2}\text{ref.})^{1/2} \quad (2)$$

where E (mv) is the sensor open circuit emf in millivolts, T is the absolute temperature in °K and $p_{o_2}$ ox. and $p_{o_2}$ ref. are the equilibrium oxygen partial pressures at the oxide and reference electrodes respectively. Combining equations (1) and (2) yields the following expression that relates the oxygen partial pressures at the oxide and reference electrodes to the activity of the oxide in the slag:

$$\log a_{ox.} = \frac{10.08 \cdot E}{T} + \log\left(\frac{p_{o_2}\text{ref.}}{p_{o_2}^o ox.}\right)^{1/2} \quad (3)$$

The values of $p_{o_2}^o$ ox. and $p_{o_2}$ ref. are constants for a particular electrode couple. The thermochemical data used for calculating the constants $p_{o_2}^o$ ox. and $p_{o_2}$ ref. for the electrode couples of the preferred embodiments are drawn from Baron, I., and Knacke, O., "Thermochemical Properties of Inorganic Substances", Springer-Verlag, Berlin, 1973; Baron, I., Knacke, O. and Kubaschewski, O., "Thermochemical Properties of Inorganic Substances, Supplement", Springer-Verlag, Berlin, 1977; Turkdogan, E. T., *Ironmaking and Steelmaking*, 1993, 20(6), 469; and Hultgren, R., Desai, P. D., Hawkins, D. T., Gleiser, M. and Kelley, K. K., "Selected Values of Thermodynamic properties of Binary Alloys", ASTM, 1973.

An electrochemical sensor having a galvanic action for measuring the activity of iron oxide in various types of molten slags in equilibrium with iron is disclosed in U.S. Pat. No. 4,657,641. The patent discloses a reference electrode 4 of a powder mixture of ($Mo+MoO_2$) or ($Cr+Cr_2O_3$) incased in a stabilized $ZrO_2$ thimble electrolyte 3, and a Mo lead line 6 immersed in the molten metal to complete the electric circuit (see particularly FIGS. 1 and 10). With this type of sensor, i.e. having a solid electrolyte interposed between the slag and the reference electrode, the value of the $p_{o_2}$ ref at the slag-electrolyte interface is ill defined because it is a function of both the oxygen transfer rate across the electrolyte wall (a diffusion process) to or from the reference electrode and a redox reaction at the slag-electrolyte interface.

Another slag-FeO sensor for measuring the in-situ oxygen activity of slag has been developed by Heraeus Electro-Nite. The sensor, known as Quick-Slag® comprises a $Cr+Cr_2O_3$ reference electrode encased in a $ZrO_2+MgO$ solid electrolyte. In use, the sensor is immersed through the slag layer into the molten steel bath, a small amount of slag being collected on the solid electrolyte resulting in a slag/metal interface on the sensor. The sensor has been extensively tested, as reported by Meszaros, G. A. et al., "Implementation of a Ladle Slag Oxygen Activity Sensor to Optimize Ladle Slag Practices at the U.S. Steel Mon Valley Works", *Iron and Steelmaker*, 1997, 24(7), 33. The test results of the sensor show the sensor emf output increasing as FeO content of the slag increases, although the measurements do not register the theoretical relationship between the FeO activity and the sensor emf readings.

While the above described sensors are available for measuring the activity of FeO in slag, there is a need in the art for a sensor which more accurately determines the activity of FeO in slag, and preferably, is also able to simultaneously measure the activity of more than one kind of oxide present in the slag. By recognizing that the molten slag itself is an electrolyte, the need for a solid electrolyte is eliminated in constructing an electrochemical sensor. Accordingly, by the eliminating the uncertainty in the value of $p_{o_2}$ ref. caused by the diffusion process through the solid electrolyte, the accuracy of the sensor is increased.

BRIEF SUMMARY OF THE INVENTION

Briefly stated the present invention provides an electrochemical sensor for insertion into slag for determining an activity of a metal oxide in the slag. The sensor includes a reference electrode comprising a mixture of a metal alloy and a metal oxide, the metal alloy and the metal oxide each being exposed on a surface of the reference electrode. The sensor also includes at least one oxide electrode comprising a mixture of a metal alloy and a metal oxide different from the mixture of the reference electrode, the metal alloy and the metal oxide of the oxide electrode each being exposed on a surface of the oxide electrode. The sensor further includes a refractory housing holding the reference electrode and the at least one oxide electrode wherein the reference electrode and the at least one oxide electrode extend from the refractory housing such that the surface of the reference electrode and the surface of the oxide electrode are each in direct contact with the slag when the sensor is inserted into the slag.

The present invention also provides a sensor having an electrochemical reaction when inserted into molten slag for determining an activity of a metal oxide in the slag. The sensor includes a reference electrode comprising a mixture of a metal alloy and a metal oxide; at least one oxide electrode comprising a mixture of a metal alloy and a metal oxide different from the mixture of the reference electrode; and a refractory housing holding the reference electrode and the oxide electrode in direct contact with the slag when the sensor is inserted into the slag, wherein the electrochemical reaction of the sensor relies on the electrolytic properties of the molten slag.

The present invention further provides a method for determining the activity of at least one metallic oxide in slag. The method comprises the steps of inserting an electrochemical sensor having a reference electrode and at least one oxide electrode into the slag such that the reference electrode and each oxide electrode are in direct contact with the slag and not in contact with molten metal beneath the slag; measuring a temperature of the slag; and measuring an electromotive force between the reference electrode and each oxide electrode.

BRIEF DESCRIPTION OF THE SEVERAL VIEWS OF THE DRAWINGS

The foregoing summary as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 3b. is a schematic cross-sectional view of the third preferred embodiment taken along lines 3b–3b of FIG. 3a;

DETAILED DESCRIPTION OF THE INVENTION

Figure 1:
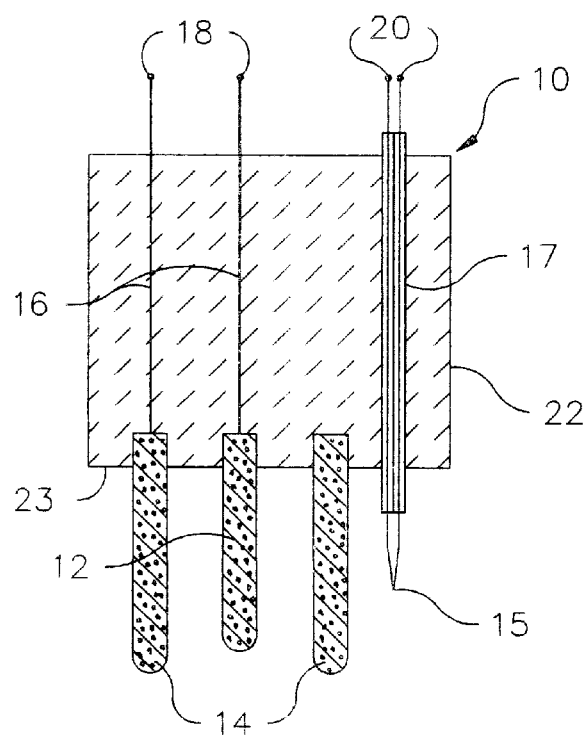
FIG. 1 is a schematic cross-sectional view of a first preferred embodiment of a slag-oxide emf sensor including a tubular reference electrode.

Referring to the drawings, wherein like numerals are used to indicate like elements throughout the several figures and the use of the indefinite article "a" may indicate a quantity of one or more than one of an element, there is shown in FIG. 1 a first preferred embodiment of a slag oxygen sensor 10 for determining the activity of metal oxides in a slag. The oxygen sensor 10 comprises a single reference electrode 14, a single oxide electrode 12 and a refractory housing 22 holding the reference electrode 14 and the oxide electrode 12.

In the first preferred embodiment, the reference electrode 14 and the oxide electrode 12 include primarily mixtures of a metal and a metal oxide (metal+metal oxide). There are but a few metal+metal oxide mixtures having a sufficiently high melting point which are resistant to molten slags during preferably short immersion times in slag and which are also suitable as the reference electrode 14. In the first preferred embodiment, the reference electrode 14 includes primarily Ta+Ta$_2$O$_5$ having a melting point of about 1877° C. The oxygen potential at the slag-reference electrode interface is defined by the reaction equilibrium:

$$\tfrac{1}{5}Ta_2O_5(s) = \tfrac{2}{5}Ta(s) + \tfrac{1}{2}O_2(g). \tag{4}$$

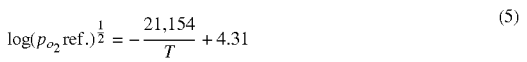

$$\log(p_{o_2}\text{ref.})^{\tfrac{1}{2}} = -\frac{21{,}154}{T} + 4.31 \tag{5}$$

Alternatively the reference electrode 14 may be formed primarily of a metal alloy and a metal oxide Ti(Mo)+TiO$_2$ mixture. The melting point of the pure metal Ti is only about 1660° C. and that of TiO$_2$ (rutile) is about 1870° C. To ensure integrity of the electrode at high steelmaking temperatures, an alloy of 50% Ti (Mo) with a melting point of about 1950° C. may be used. For the Ti(Mo)+TiO$_2$ reference electrode, where the activity, a$_{Ti}$, of the titanium in the solid alloy is 0.65, the oxygen potential at the slag-electrode interface is defined by the reaction equilibrium:

$$\tfrac{1}{2}TiO_2(s) = \tfrac{1}{2}Ti/Mo(s) + \tfrac{1}{2}O_2(g) \tag{6}$$

$$\log(p_{o_2}\text{ref.})^{\tfrac{1}{2}} = -\frac{24{,}577}{T} + 4.73 \tag{7}$$

It will be appreciated by those skilled in the art that the reference electrode is not limited to Ta+Ta$_2$O$_5$ and Ti(Mo)+TiO$_2$ mixtures. Other metal+metal oxide mixtures having a melting point greater than the temperature of the molten slag and not susceptible to chemical attack by the slag could be used for the reference electrode 14. For example, $Cr+Cr_2O_3$, could be used for the reference electrode 14, and still be within the spirit and scope of the invention.

In the first preferred embodiment of the slag oxygen sensor 10, the composition of the oxide electrode 12 is specifically chosen to react with one of the several metal oxides in the slag for which the existence of a relationship between the metal oxide's activity in the slag and the concentration of the metal oxide in the slag has been established. Similar to the reference electrodes 14, the materials chosen for use as the sensor oxide electrodes 12 must be able to withstand the high temperatures of the slag and not be susceptible to chemical attack by the slag. In the first preferred embodiment, the oxide electrode 12 which reacts to FeO, is preferably an alloy of 10 wt % Fe–Mo which has a melting point of about 1850° C. (where the expression X % wt Y represents the percentage of X by weight of Y in the alloy). For the reaction equilibrium at the slag-oxide electrode interface the oxygen potential is defined by the reaction equilibrium:

$$FeO(\text{in slag}) = Fe/Mo(s) + \tfrac{1}{2}O_2(g) \tag{8}$$

$$\log\left[\frac{a_{Fe}}{a_{FeO}} \cdot (p_{O_2}ox.)^{\tfrac{1}{2}}\right] = -\frac{11{,}058}{T} + 1.76 \tag{9}$$

With the assumption that the iron activity, $a_{Fe}$, in the Fe/Mo solid solution equals 0.1, $$\log(p_{O_2}ox.)^{\tfrac{1}{2}} = -\frac{11{,}058}{T} + 2.76 + \log a_{FeO}, \tag{10}$$

where $a_{FeO}$ is with respect to pure liquid FeO as the standard state. The following theoretical $a_{FeO}$ vs. sensor emf (in mv) relations are obtained by inserting equation (10) into equation (2) together with either equation (5) and (7), depending on the material of the reference electrode 14.

For a $Ta+Ta_2O_5$ reference electrode:

$$\log a_{FeO} = -\frac{10{,}096 - 10.08 \cdot E}{T} + 1.55. \tag{11}$$

For a $Ti(Mo)+TiO_2$ reference electrode:

$$\log a_{FeO} = -\frac{13{,}520 - 10.08 \cdot E}{T} + 1.97. \tag{12}$$

Alternatively an oxide electrode 12 may be comprised of a mixture of $Cr+FeCr_2O_4$ for which the slag-electrode reaction is:

$$\tfrac{1}{3}FeCr_2O_4(s) = \tfrac{1}{3}FeO(\text{in slag}) + \tfrac{2}{3}Cr(s) + \tfrac{1}{2}O_2(g) \tag{13}$$

and for which the equilibrium relation is:

$$\log(p_{O_2}ox.)^{\tfrac{1}{2}} = -\frac{21{,}160}{T} + 4.99 - \tfrac{1}{3}\log a_{FeO} \tag{14}$$

Inserting equations (10) and (14) into equation (2) gives:

$$\log a_{FeO} = -\frac{7577 - 7.56 \cdot E}{T} + 1.67. \tag{15}$$

Figure 4:
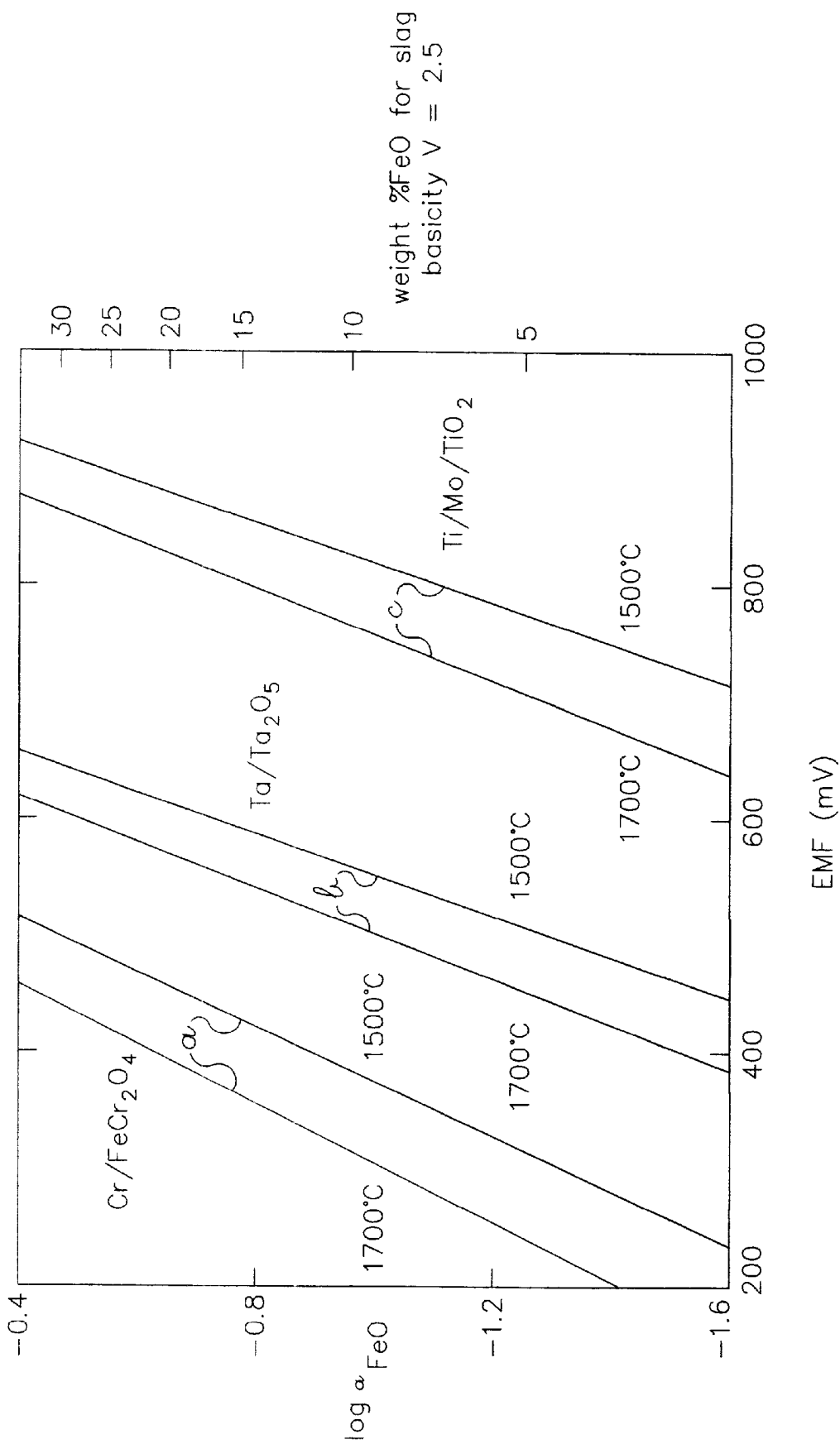
FIG. 4 is a plot of an open circuit electromotive force (emf) of an Fe+Mo electrode as a function of the activity of FeO and the corresponding weight % FeO in slag.

FIG. 4 is a plot of an open circuit electromotive force (emf) of an Fe+Mo electrode as a function of the activity of FeO and the corresponding weight % FeO (concentration of FeO) in slag. Curves a, b and c correspond to equations (15), (11) and (12) respectively for slag temperatures of 1500° C. and 1700° C.

For an average slag basicity of %CaO/%$SiO_2$=2.5, the activity coefficient γFeO is about 1.33 for which the weight concentrations of FeO in the slag, corresponding to the FeO activities, are marked on the right hand ordinate of FIG. 4. The values of $\gamma_{FeO}$ are taken from Turkdogan, E. T., *Proc. of the Ethem T. Turkdogan Symposium*, 1994, pp. 253–269. The Iron and Steel Society, Warrendale, Pa., USA, and are given in Table I below for lime-saturated steelmaking slags where the FeO contents are within the indicated ranges.

TABLE I

| V = % CaO/% $SiO_2$ | γFeO | weight % FeO |
|---|---|---|
| 2.0 | 2.00 | 2–8 |
| 2.5 | 1.33 | 11–20 |
| 3.0 | 1.11 | 17–30 |
| 3.5 | 0.98 | 25–36 |
| 4.0 | 0.87 | 30–40 |

In the first preferred embodiment of the slag $SiO_2$ sensor 10, the oxide electrode considered suitable is a solid alloy mixture preferably of $Ta+Ta_2Si$.
The equilibrium relation is:

$$Ta(s) + \tfrac{1}{2}SiO_2(\text{in slag}) = \tfrac{1}{2}Ta_2Si(s) + \tfrac{1}{2}O_2(g) \tag{16}$$

$$\log(p_{O_2}ox.)^{\tfrac{1}{2}} = -\frac{20{,}210}{T} + 4.52 + \tfrac{1}{2}\log a_{SiO_2} \tag{17}$$

Equation (17) together with equation (5) for the reference electrode $Ta+Ta_2O_5$ gives:

$$\log a_{SiO_2} = -\frac{1888 - 20.16 \cdot E}{T} - 0.42 \tag{18}$$

With the reference electrode $Ti(Mo)+TiO_2$ in equation (7), the following relation is obtained:

$$\log a_{SiO_2} = -\frac{8734 - 20.16 \cdot E}{T} + 0.42 \tag{19}$$

Figure 5:
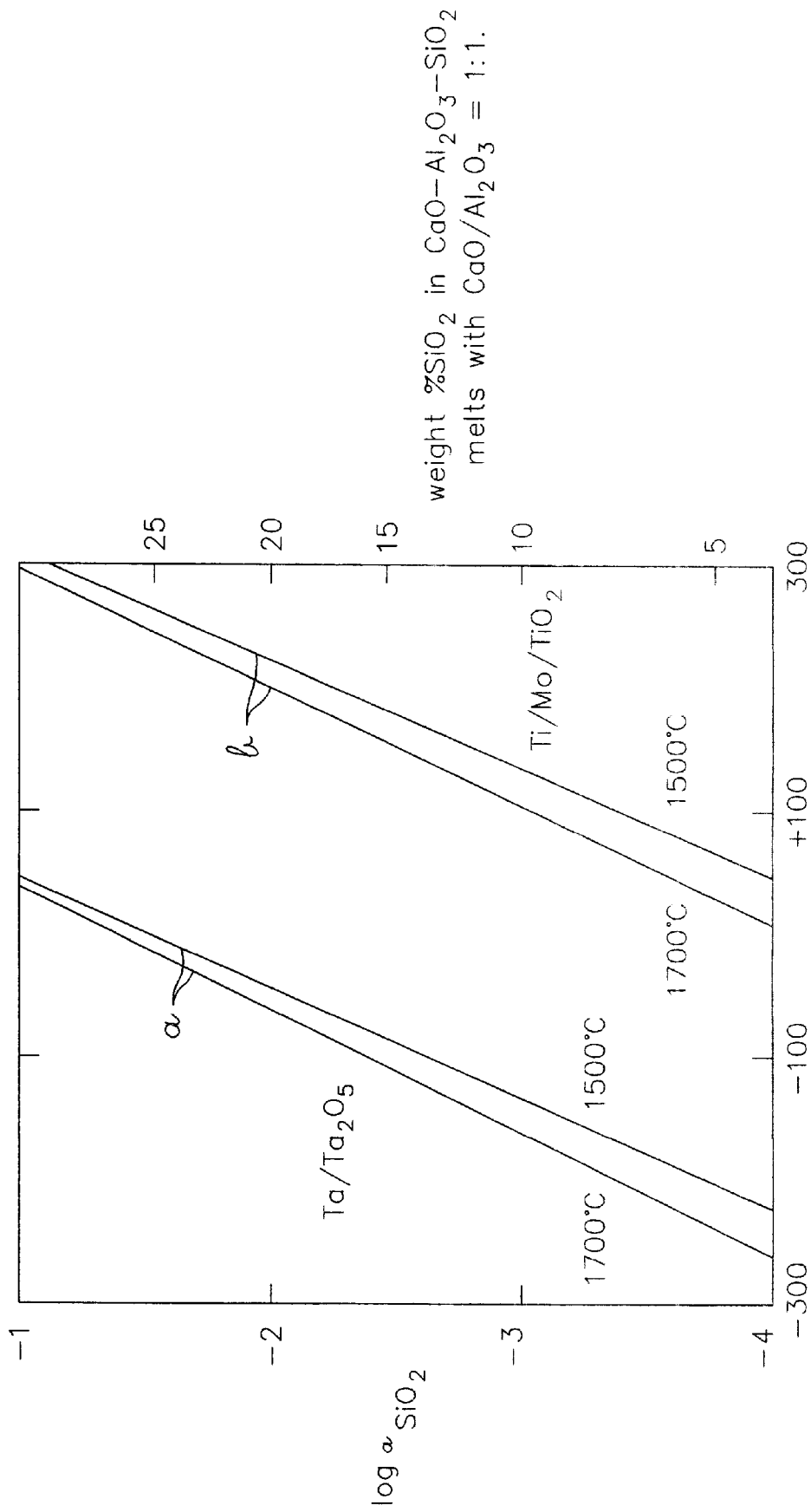
FIG. 5 is a plot of an open circuit electromotive force (emf) of an Ta+Ta$_2$Si electrode as a function of the activity of Sio$_2$ and the corresponding weight % SiO$_2$ in slag.

FIG. 5 is a plot of an open circuit electromotive force (emf) of an $Ta+Ta_2Si$ electrode as a function of the activity of $SiO_2$ and the corresponding weight % $SiO_2$ in slag. Curves a and b correspond to equations (18) and (19) respectively for slag temperatures of 1500° C. and 1700° C.

The weight concentrations of $SiO_2$ on the right hand ordinate of FIG. 5, for the corresponding activities, are for the CaO—$Al_2O_3$—$SiO_2$ melts at 1600° C. with CaO/$Al_2O_3$= 1:1 lusing experimental data taken from Rein, R. H. and Chipman, J., *Trans. Met. Soc. AIME*, 1965, 233 415.

In the first preferred embodiment for a slag-CaO sensor, the preferred oxide electrode is a sintered mixture of 50% Ti-Mo alloy ($a_{Ti}$=0.65) and the compound $CaTiO_3$ for which the reaction equilibrium is:

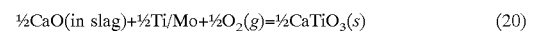
$$\tfrac{1}{2}CaO(\text{in slag}) + \tfrac{1}{2}Ti/Mo + \tfrac{1}{2}O_2(g) = \tfrac{1}{2}CaTiO_3(s) \tag{20}$$

$$\log(p_{O_2}ox.)^{\frac{1}{2}} = -\frac{26{,}400}{T} + 4.42 - \frac{1}{2}\log a_{CaO} \quad (21)$$

The following equations are obtained for the two reference electrodes considered. For a Ta+Ta$_2$O$_5$ reference electrode:

$$\log a_{CaO} = -\frac{10{,}492 - 20.16 \cdot E}{T} + 0.22. \quad (22)$$

For a Ti(Mo)+TiO$_2$ reference electrode:

$$\log a_{CaO} = -\frac{3.646 - 20.16 \cdot E}{T} - 0.62. \quad (23)$$

Figure 6:
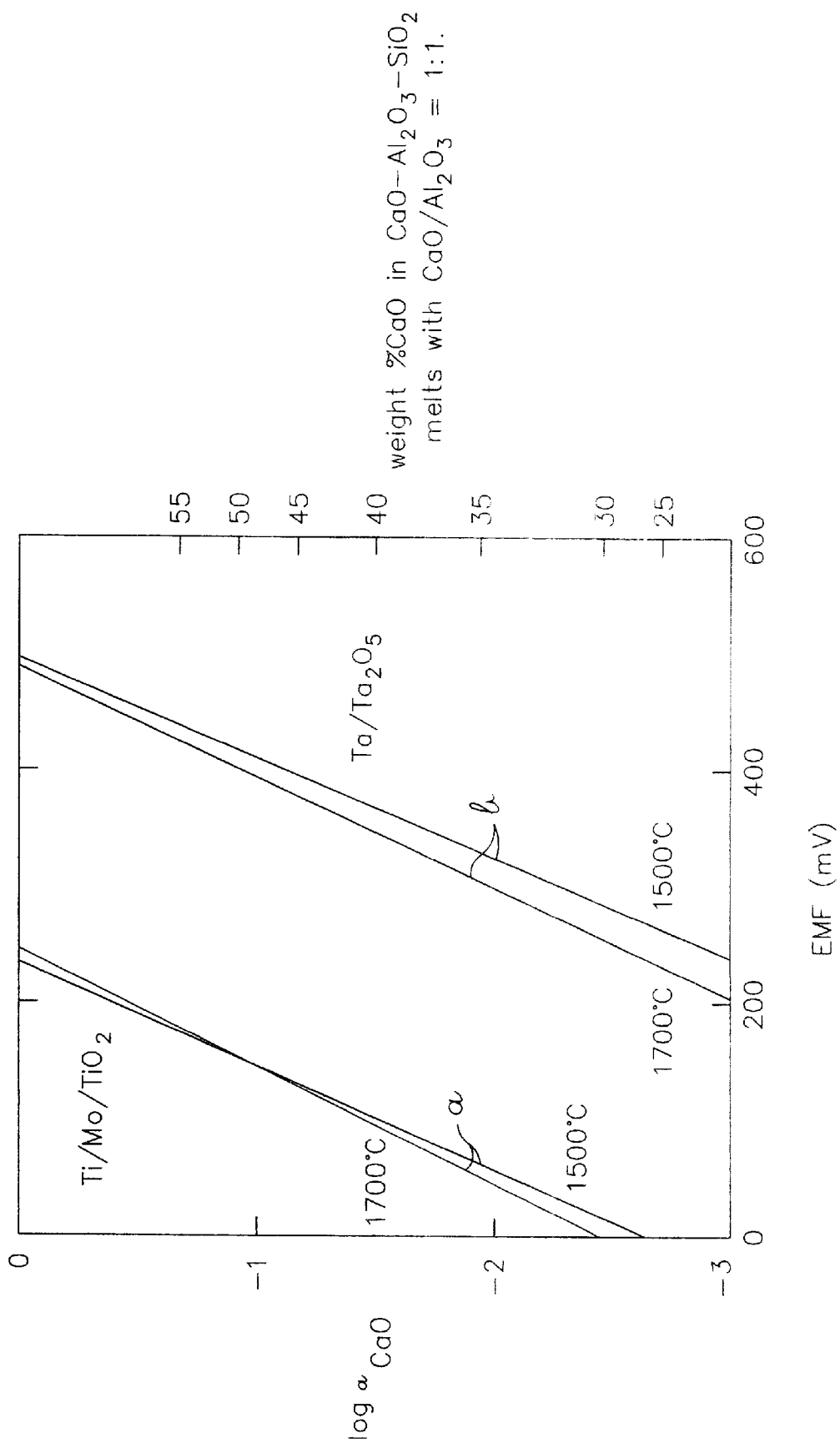
FIG. 6 is a plot of an open circuit electromotive force (emf) of a Ti(Mo)+CaTiO$_3$ electrode as a function of the activity of CaO and the corresponding weight % CaO in slag.

FIG. 6 is a plot of an open circuit electromotive force (emf) of a Ti(Mo)+CaTiO$_3$ electrode as a function of the activity of CaO and the corresponding weight % CaO in slag. Curves a and b correspond to equations (22) and (23) respectively for slag temperatures of 1500° C. and 1700° C. The temperature effect is practically negligible for the CaO sensor. The weight concentrations of CaO marked on the right hand ordinate in FIG. 6 are for the CaO—Al$_2$O$_3$—SiO$_2$ melts with CaO/Al$_2$O$_3$=1:1, using experimental data taken from Rein, R. H. and Chipman, J., *Trans. Met. Soc. AIME*, 1965, 233, 415.

In the first preferred embodiment, the sensor electrodes 12, 14 are comprised of an intimate mixture of metal alloys and oxide compounds of fine particle size. The mixture is preferably compressed to form the desired shape, e.g. tubular, strip or rod shape and sintered at a high temperature in oxygen and nitrogen-free dry argon. In the first preferred embodiment, the diameters of the metal alloy and metal oxide particles preferably range in diameter from about 0.037 mm to about 0.105 mm. The temperature at which the sintering takes place is preferably in the range of about 1200° C. to about 1400° C. The method of manufacturing the electrodes 12, 14 is well known to those in the ceramics industry who are skilled in the art of making cermets for high temperature applications and need not be repeated here for a full understanding of the invention. Alternatively, the electrodes 12, 14 can be manufactured by plasma spraying of the mixed particle ingredients of the oxide electrode 12 and the reference electrode 14 onto a Mo support of desired shape, e.g. tubular, strip or wire form. It should be noted that both the metal alloy and metal oxide components of the electrodes must be exposed on the surface of the electrodes to make direct contact with the slag for proper functioning of the electrodes 12, 14. A sintered or plasma sprayed electrode 12, 14 does not have a glazed surface masking the components of the electrode 12, 14, thus properly exposing both the metal alloy and the metal oxide components of the mixture to the slag. Another important point to note is that the electrodes 12, 14 in the slag oxide sensors should be electron conductors, which is the case with electrodes incorporating metallic elements.

The first preferred embodiment also includes a refractory housing 22. In the first preferred embodiment the refractory housing 22 is made of cast alumina. As will be appreciated by one skilled in the art other similar materials capable of being cast and having a high dimensional stability at the temperature of the slag, such as silica sand, may be used within the spirit and scope of the invention. The method of manufacturing the refractory housing 22 is well known to those skilled in the art and need not be described for a full understanding of the invention. The refractory housing 22 includes electrode cavities into which are fit the electrodes 12, 14, and Mo wires 16 which connect the reference electrode 14 and the oxide electrode 12 to an external voltage measuring means such as a digital voltmeter via electrode terminals 18. The housing also includes a cavity for holding a conventional thermocouple 17. The thermocouple 17 has a bare thermocouple junction 15 which preferably extends below the bottom 23 of the refractory housing 22 so as to be proximate to the electrodes 12, 14 and in direct contact with the slag. The thermocouple 17 also has a pair of terminals 20 for connection to a conventional means for measuring the emf generated by the thermocouple 17. In the first preferred embodiment the thermocouple metals are preferably one or more of Mo, W, Nb and Ir or similar materials, selected to have a melting point higher than the temperature of the slag and to be resistant to slag attack.

In the first preferred embodiment, the reference electrode 14 has a tubular shape of about 10 mm inside diameter and extends about 15 mm from the bottom 23 of the refractory housing 22. The oxide electrode 12 is located within the circumference of the tubular shaped reference electrode 14 and extends somewhat less than about 15 mm from the bottom 23 of the refractory housing 22. The electrodes 12, 14 are about 2 mm thick. The electrodes 12, 14 are preferably designed to have a low thermal mass to allow the slag oxygen sensor to come rapidly to thermal equilibrium. As will be appreciated by those skilled in the art based on this disclosure, the electrodes 12, 14 are not limited to a diameter of 10 mm, a length of 15 mm or a thickness of 2 mm. The electrodes 12, 14 could be of greater or lesser diameter, length and thickness and still be within the spirit and scope of the invention.

Figure 2:
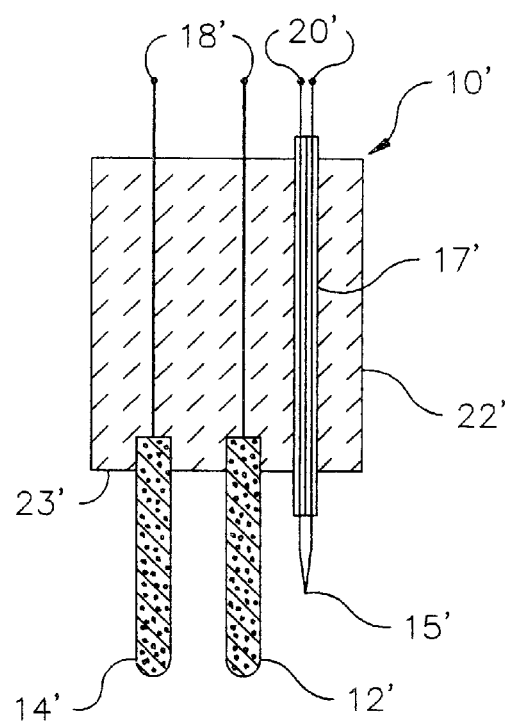
FIG. 2 is a schematic cross-sectional view of a second preferred embodiment of a slag-oxide emf sensor including a rod shaped reference electrode.

A second preferred embodiment of the slag oxygen sensor 10, shown in FIG. 2, is identical to the first preferred embodiment except that instead of the reference electrode 14 being tubular, it is rod shaped and spaced about 5 mm from the oxide electrode 12.

Figure 3A:
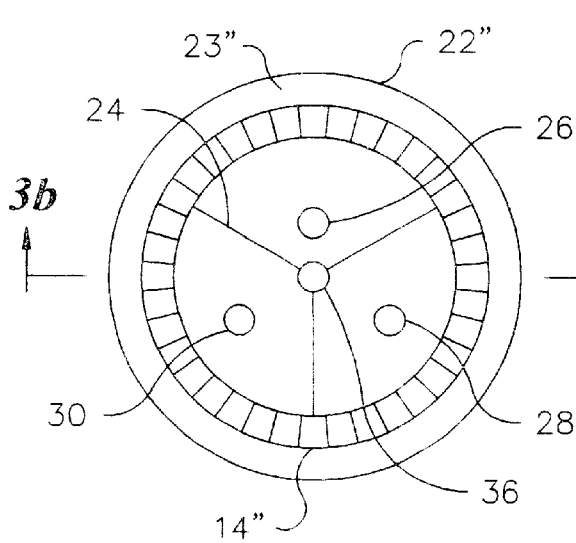
FIG. 3a. is a schematic bottom plan view of a third preferred embodiment of a slag-oxygen sensor including three oxide electrodes and a tubular reference electrode.
Figure 3B:
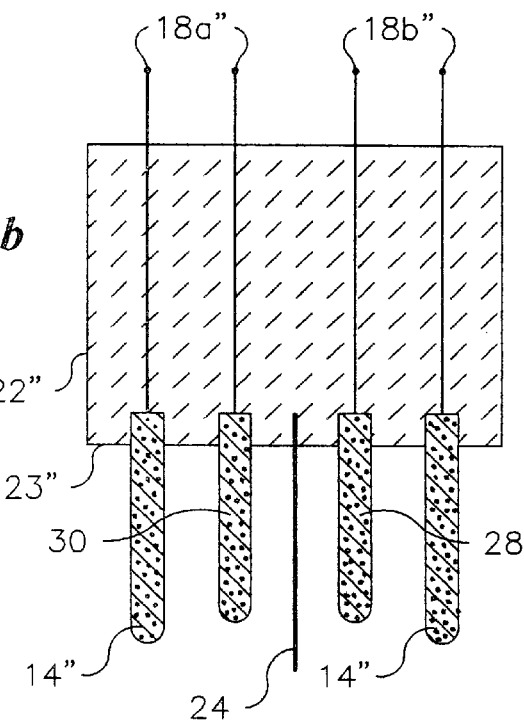

A third preferred embodiment of the slag oxygen sensor 10 is capable of simultaneously measuring the activity of two or more metal oxides in the slag with a single immersion of the slag-oxygen sensor 10 in the molten slag. In the third preferred embodiment, shown in FIGS. 3a and 3b, there is mounted a CaO electrode 26, an SiO$_2$ electrode 28 and a FeO electrode 30 extending from the refractory housing bottom 23". The electrodes 26, 28, 30 are separated from each other by an Mo strip divider 24. A centrally located cavity 36 holds the thermocouple 17. The reference electrode 14" is shaped as a ring having an inside diameter of about 20 mm. and a thickness of about 2 mm. The activity of each metal oxide is determined by measuring the difference in emf between the respective oxide electrode terminals and the reference electrode terminal 18a", 18b" and 18c" (18c" not shown).

In use, the slag oxygen sensor 10 is attached to a sub-lance through which electrically conductive wires carry the emf generated by the oxide electrode-reference electrode pairs 12, 14 and the emf generated by the thermocouple 17. The slag oxygen sensor 10 is inserted into the slag layer such that the reference electrode 14 and each oxide electrode 12 are in direct contact with the slag and not in contact with the molten metal. In the first and second preferred embodiments, the activity of the metal oxide in the slag is determined by measuring the emf generated between the reference electrode 14 and the oxide electrode 12. In the third preferred embodiment, the emf between the reference electrode 14" and each oxide electrode 26, 28 30 is measured. Simultaneously with the measurement of the emf of each electrode pair 12, 14, the emf generated by the thermocouple 17 is measured to determine the temperature of the slag proximate to the slag oxygen sensor 10. Based on the measured electrode emfs and the temperature of the slag, the respective activity and concentration of the FeO, CaO and SiO$_2$ in the slag are calculated using, for example, the curves provided in FIGS. 4, 5 and 6. It will be appreciated by those skilled in the art that the precise relationships between the generated emfs, the metal oxide activities in the molten slag and the metal oxide concentrations in the molten slag may vary for different refining conditions. Accordingly, data set forth in the drawings are specific to the conditions shown. However, as will be further appreciated by those skilled in the art, the sensor 10 may be applied in determining the activity and concentrations of other molten slag compositions, dependent only upon the availability or generation of appropriate thermochemical data.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims

What is claimed is:

1. An electrochemical sensor for insertion into molten slag for determining an activity of a metal oxide in the slag comprising:

a reference electrode comprising a mixture of (i) a metal or a metal alloy and (ii) a metal oxide, the metal or the metal alloy and the metal oxide each being exposed on a surface of the reference electrode;

at least one oxide electrode comprising (i) a metal alloy, (ii) a mixture of a metal and a metal oxide or (iii) a mixture of a metal and a metal silicide different from the mixture of the reference electrode, the metal alloy, the metal oxide and the metal silicide of the oxide electrode each being exposed on a surface of the oxide electrode; and a refractory housing holding the reference electrode and the at least one oxide electrode wherein the reference electrode and the at least one oxide electrode extend from within the refractory housing such that the surface of the reference electrode and the surface of the oxide electrode are each in direct contact with the molten slag when the sensor is inserted into the slag.

2. An electrochemical sensor according to claim 1 wherein the reference electrode and each oxide electrode are electron conductors.

3. An electrochemical sensor according to claim 1 wherein a mixture of the reference electrode is selected from the group consisting of $Cr+Cr_2O_3$, $Ta+Ta_2O_5$ and $Ti(Mo)+TiO_2$.

4. An electrochemical sensor according to claim 1 wherein a mixture of the oxide electrode suitable for determining the amount of FeO in the slag is selected from the group consisting of 10% Fe—Mo and $Cr+FeCr_2O_4$.

5. An electrochemical sensor according to claim 1 wherein a mixture of the oxide electrode for determining the amount of $SiO_2$ in the slag comprises $Ta+Ta_2Si$.

6. An electrochemical sensor according to claim 1 wherein a mixture of the oxide electrode for determining the amount of CaO in the slag comprises 50% Ti—Mo+$CaTiO_3$.

7. An electrochemical sensor according to claim 1 further including a bare thermocouple junction b in direct contact with the slag.

8. An electrochemical sensor according to claim 1 wherein the reference electrode is tubular, a portion of the at least one oxide electrode being located within the circumference of the reference electrode.

9. An electrochemical sensor according to claim 8, the sensor comprising at least two oxide electrodes, the at least two oxide electrodes being separated from each other by a metallic strip extending from the refractory housing.

10. A sensor having an electrochemical reaction when inserted into molten slag for determining an activity of a metal oxide in the slag comprising:

a reference electrode comprising a mixture of (i) a metal or a metal alloy and (ii) a metal oxide;

at least one oxide electrode comprising (i) a metal alloy, (ii) a mixture of a metal and a metal oxide or (iii) a mixture of a metal and a metal silicide different from the mixture of the reference electrode; and a refractory housing holding the reference electrode and the oxide electrode, said electrodes extending from within the refractory housing and in direct contact with the molten slag when the sensor is inserted into the slag, wherein the electrochemical reaction of the sensor relies on the electrolytic properties of the molten slag.

* * * * *